United States Patent [19]

Kirlin et al.

[11] Patent Number: 5,677,002
[45] Date of Patent: Oct. 14, 1997

[54] CHEMICAL VAPOR DEPOSITION OF TANTALUM- OR NIOBIUM-CONTAINING COATINGS

[75] Inventors: Peter S. Kirlin; Brian A. Vaartstra, both of Bethel, Conn.; Douglas Gordon, Salt Lake City, Utah; Timothy E. Glassman, Danbury, Conn.

[73] Assignee: Advanced Technology Materials, Danbury, Conn.

[21] Appl. No.: 453,380

[22] Filed: May 30, 1995

Related U.S. Application Data

[62] Division of Ser. No. 307,316, Sep. 16, 1994.
[51] Int. Cl.$^6$ ..................... C23C 16/00
[52] U.S. Cl. ............... 427/248.1; 427/255.1; 427/255.2; 427/255.3; 427/314; 427/126.3
[58] Field of Search ............... 427/255.3, 255.2, 427/255.1, 248.1, 314, 126.3; 566/40, 42

[56] References Cited

U.S. PATENT DOCUMENTS

| | | | |
|---|---|---|---|
| 4,510,222 | 4/1985 | Okunaka et al. | 430/5 |
| 5,204,314 | 4/1993 | Kirlin et al. | 505/1 |
| 5,225,561 | 7/1993 | Kirlin et al. | 546/256 |
| 5,280,012 | 1/1994 | Kirlin et al. | 505/1 |
| 5,412,129 | 5/1995 | DiCarolis | 556/40 |
| 5,527,567 | 6/1996 | Desu et al. | 427/573 |

FOREIGN PATENT DOCUMENTS

3447635A1  7/1985  Germany.

OTHER PUBLICATIONS

Deutscher, R.L.; Kepert, D.L., "Eight Coordinate Tetrakis–Chelate Complexes of Niobium(IV) and Tantalum(IV)," Inorg. Chim. Acta (1970), 4, 645–650.

Kapoor, P.N.; Mehrotra, R.C., "Reactions of Niobium and Tantalum Pentaethoxides with β–Diketones," J. Less–Common Metals (1965), 8, 339–46.

Ainger, F.W. et al., "Deposition of Ferroelectric Oxides by MOCVD." Prog. Crystal Growth Charact. (1991), 22, 183–187.

Narula et al., "Prepn and Characterizn of Niobium(V) β–Diketonates," Synth. React. Inorg. Met.–Org. Chem (1983), 13, 1–19.

Narula et al., "Prepn and Characterizn of Tantalum(V) β–Diketonates," Synth. React. Inorg. Met.–Org. Chem (1983), 13, 887–98.

Mehrotra et al, Aust. J. Chem., 1966, 19, pp. 2079–2081.

*Primary Examiner*—Roy V. King
*Attorney, Agent, or Firm*—Janet Elliott; Steven J. Hultquist

[57] ABSTRACT

Niobium and tantalum compounds suitable for use as chemical vapor deposition source reagents, and a process for depositing niobium- or tantalum-containing coatings using the compounds. The compounds have formula

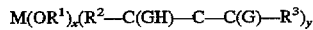

$M(OR^1)_x(R^2-C(GH)-C-C(G)-R^3)_y$ wherein M is tantalum or niobium; G is oxygen or sulfur; and $R^1$, $R^2$, and $R^3$ are independently selected hydrocarbyl, fluoroalkyl or alkoxy groups,

20 Claims, 1 Drawing Sheet

FIGURE
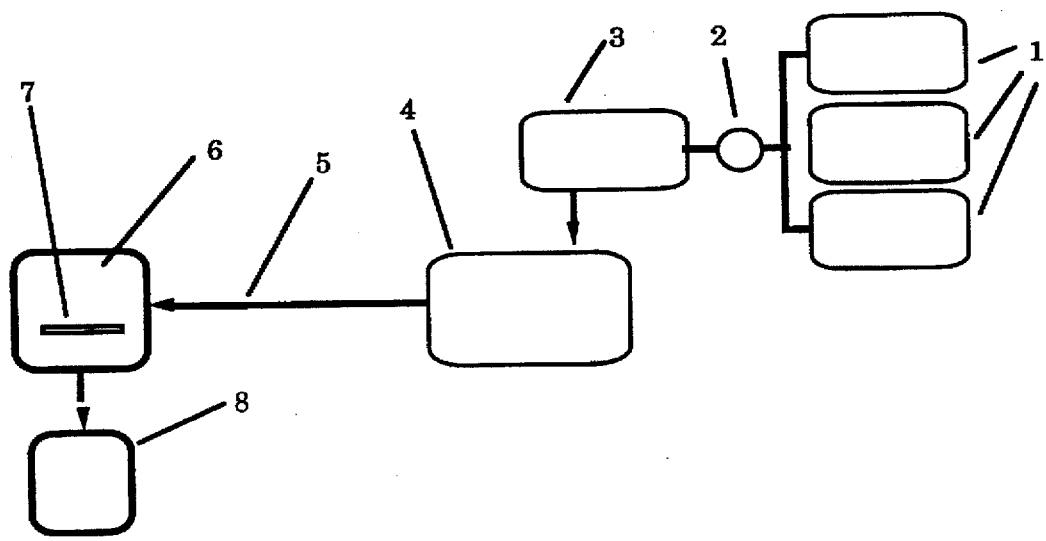

CHEMICAL VAPOR DEPOSITION OF TANTALUM- OR NIOBIUM-CONTAINING COATINGS

This is a division of U.S. application Ser. No. 08/307,316 filed Sep. 16, 1994.

BACKGROUND OF THE INVENTION

1. Field of the Invention

This invention relates to niobium and tantalum compounds useful as source reagents or precursors in chemical vapor deposition (CVD) processes such as those employed in the fabrication of ferroelectric and other oxide thin films.

2. Description of the Related Art

Many refractory materials have been identified as having unique materials properties. In particular, there are numerous applications for niobium- and tantalum-containing refractory oxide materials. A number of compounds incorporate these elements as the main constituents, including niobates and tantalates (*Principals and applications of ferroelectrics and related materials*, Lines, M. E., Glass, A. M., Clarendon Press, Oxford 1977, Appendix F). Nb is well known as a donor dopant as well in both ceramics and thin films. $Ba_xSr_{5-x}Nb_{10}O_{30}$ (where x ranges from 1.3 to 2.7) is a photonic material whose index of refraction changes as a function of applied electric field and also as a function of the intensity of light upon it. Refractory oxides such as $Ta_2O_5$ are seeing expanded use in the microelectronics industry; $Ta_2O_5$ is now being used as a thin-film capacitor material whose use may enable higher density memory devices to be fabricated.

Classes of ferroelectric materials may be described by their crystal structures; an example is the tungsten-bronze group of which strontium barium niobate $Ba_xSr_{5-x}Nb_{10}O_{30}$ is the archetype. Its predominant use is as an electrooptic material.

A second class of ferroelectrics are the layer-structure oxides of which $SrBi_2Ta_2O_9$ and $SrBi_2Nb_2O_9$ have received considerable recent attention for uses as non-volatile ferroelectric random access memories (NV-FRAM's) for computers. Thin films of $PbZr_{1-x}Ti_xO_3$ (PZT) have been the focus of extensive research in this area. One of the primary obstacles encountered in using the ferroelectric effect for information storage is the gradual decrease in remanent polarization after many cycles of ferroelectric polarity switching the thin film. For many PZT thin films, remanent polarization has significantly degraded after $10^6$ ferroelectric switching cycles, while films of $SrBi_2Ta_2O_9$ and $SrBi_2Nb_2O_9$ have been shown to have superior properties as high as $10^9$ cycles.

A third class of ferroelectrics is known as relaxors, which may have the perovskite structure and are characterized by nano-scale heterogeneities that result in frequency dependence of the dielectric constant vs. temperature relationships. The most well known relaxor is $PbMg_{1/3}Nb_{2/3}O_3$, which is widely used in electro-mechanical applications because of its large electrostrictive effect. It is also used as a dielectric in capacitors since it can be processed at temperatures somewhat lower than $BaTiO_3$ compositions and it has a high dielectric constant. A second relaxor compound is $PbSc_{1-x}Ta_xO_3$ whose predominant use has been for pyroelectric IR detectors.

Nb is also a well known donor dopant in $BaTiO_3$ and PZT thin films. This element is added because the predominant electrical conduction mechanism in these compounds is O vacancy migration, and dopants of this kind reduce the O vacancy concentrations. Mobile oxygen vacancies are believed to play a part in fatigue in ferroelectric computer memories, and $BaTi_{0.97}Nb_{0.03}O_{3+\delta}$ films have been made to investigate possible improvement in this property; significant improvement is observed.

Many of the potential applications of these niobium- and tantalum-containing refractory oxide materials require their use in thin film, coating, or layer form. The films or layers may also be advantageously epitaxially related to the substrate upon which they are formed. Applications in which the niobium- and tantalum-containing materials may need to be deposited in film or layer form include integrated circuits, switches, radiation detectors, thin film capacitors, holographic storage media, and various other microelectronic devices.

Methods for forming the thin films, coatings or layers of niobium and tantalum oxide materials include sputtering and other physical vapor deposition methods, chemical vapor deposition, and sol-gel processing. The latter two methods are particularly useful in that they can coat surfaces with complex geometries.

Chemical vapor deposition (CVD) is a particularly attractive method for forming these layers because it is readily scaled up to production runs and because the electronics industry has a wide experience and an established equipment base in the use of CVD technology which can be applied to new CVD processes. In general, the control of key variables such as stoichiometry and thickness, and the coating of a wide variety of substrate geometries is possible with CVD. Forming the thin films by CVD will permit the integration of these materials into existing device production technologies. CVD also permits the formation of layers of the refractory materials that are epitaxially related to substrates having close crystal structures.

CVD requires that the element source reagents must be sufficiently volatile to permit gas phase transport into the deposition reactor. The element source reagent must decompose in the reactor to deposit only the desired element or its oxide at the desired growth temperatures. Premature gas phase reactions leading to particulate formation must not occur, nor should the source reagent decompose in the lines before reaching the reactor deposition chamber. When compounds are to be deposited, obtaining optimal properties requires close control of stoichiometry which can be achieved if the reagents can be delivered into the reactor in a controllable fashion. In addition, the reagents must not be so chemically stable that they do not react in the deposition chamber.

Thus a desirable CVD reagent is fairly reactive and volatile. Many potentially highly useful refractory materials have in common that one or more of their components are elements, such as the Group II metals barium, calcium, or strontium, or early transition metals zirconium or helium, for which few volatile compounds well-suited for CVD are known. In many cases, the source reagents are solids whose sublimation temperature may be very close to the decomposition temperature, in which case the reagent may begin to decompose in the lines before reaching the reactor, and it will be very difficult to control the stoichiometry of the deposited films.

In other cases, the CVD reagents are liquids, but their delivery into the CVD reactor in the vapor phase has proven problematic because of problems of premature decomposition or stoichiometry control.

The problem of controlled delivery of CVD reagents into deposition reactors was addressed by the inventors in U.S.

Pat. No. 5,204,314 "Method for Delivering an Involatile Reagent in Vapor Form to a CVD Reactor," and further elaborated in U.S. patent application Ser. No. 07/927,134, "Apparatus and Method for Delivery of Involatile Reagents," filed Aug. 7, 1992 now abandoned, which hereby are incorporated herein by reference. As described and claimed in these patents, the delivery of reagents into the deposition chamber in vapor form is accomplished by providing the reagent in a liquid form, as a neat liquid or solution of a solid or a liquid compound, and flowing the reagent liquid onto a flash vaporization matrix structure which is heated to a temperature sufficient to flash vaporize the reagent source liquid. A carrier gas may optionally be flowed by the flash vaporization matrix structure to form a carrier gas mixture containing the flash vaporized reagent.

In the design, of chemical vapor deposition source reagents, considerations can include solubility in the convenient and commonly used solvent systems for liquid delivery systems as described in U.S. Pat. No. 5,204,314; volatility for ease of delivery into a CVD reactor; stability to oxidation, hydrolysis, and thermal decomposition; compatibility with other CVD source reagents employed in the system for delivery of other elements of the desired oxide compound; and elemental and chemical purity.

For tantalum and niobium, the most widely used CVD source reagents have been the well-known simple alkoxides such as ethoxides and isopropoxides, e.g., $Ta(OEt)_5$, $Nb(OEt)_5$. These materials are relatively inexpensive, readily purified, and quite volatile. As liquids, they can be delivered to the CVD reactor using the liquid delivery system of U.S. Pat. No. 5,204,314. Other alkoxide compounds are readily synthesized, subject to steric limitations posed by bulky groups such as tert-butoxy.

However, as mentioned above, many of the useful tantalum- and niobium-containing refractory materials have in common that one or more of their components are elements, such as the Group II metals barium, calcium, or strontium, or early transition metals zirconium or hafnium, for which few volatile compounds well-suited for CVD are known. CVD source reagents for such elements are most advantageously complexes of the element with ligands such as beta-diketonates, polyethers, polyamines, etc. that render the complex more volatile. Examples of beta-diketonate ligands often used in such complexes include acetylacetonate (acac), tetramethylheptanedionate (thd), hexafluoroacetylacetonate (hfacac), and 1,1,1,2,2,3,3-heptafluoro-7,7-dimethyl-4,6-octanedionate (fod). Group II metal complexes suitable for use as CVD source reagents may include ether or amine ligands to enhance volatility, as in the complexes which are described in U.S. Pat. Nos. 5,225,561 and 5,280,012, the disclosures of which are hereby incorporated herein by reference.

Nonetheless, for these Group II and early transition metals, the CVD source reagent complexes as described above are still not highly volatile. Most such reagents are solids. Thus, for delivery into a CVD reactor they are typically heated to high temperatures or are warmed sufficiently to be delivered to a heated vaporizer in a solvent as described for the liquid delivery system of U.S. Pat. No. 5,204,314. Therefore, for deposition of the complex oxide compounds containing tantalum or niobium, the tantalum or niobium source reagent will be at some point combined with the source reagents for the other elements, either in solution or at elevated temperatures in the vapor phase.

Upon heating the ensemble of reagents to vaporize and deliver them to the reactor or under the high temperature conditions present in the CVD reactor, the various metal complexes may undergo ligand exchange reactions. If the products of such ligand exchange reactions are involatile, the result may be premature nucleation and formation of particulate species in the reactor, in the lines leading from the source reservoir(s) to the reactor, or in the source reservoir itself, if more than one reagent is held in the same reservoir.

An example illustrating this problem is the preparation of films of strontium bismuth tantalate and strontium bismuth niobate ($SrBi_2Ta_2O_9$ and $SrBi_2Nb_2O_9$) by CVD for use in non-volatile ferroelectric random access memories. The most commonly used strontium source reagents are beta-diketonate complexes such as $Sr(thd)_2$. Consider the following source reagent complement for deposition of $SrBi_2Ta_2O_9$:

$Sr(thd)_2$ $Ta(OEt)_5$ $Bi(Ph)_3$ (Ph=phenyl)

Upon heating a solution containing these compounds, the ethoxide ligands of the tantalum reagent exchanged with the thd ligands of the strontium reagent, leading to the formation of undesirable strontium alkoxide species that have reduced volatility and which can decompose in the vaporization zone. Alternatively, when the reagents were provided separately in bubblers, similar ligand exchange reactions occurred in the gas phase and the resulting solids clogged the gas lines.

Thus stability to ligand exchange reactions in the solvent/reagent system of choice is an important consideration. For CVD of multicomponent oxide materials, compatibility of the reagents requires resistance to ligand exchange reactions. The well-known simple alkoxides such as ethoxides, isopropoxides, and t-butoxides of tantalum and niobium, e.g., $Ta(OEt)_5$, $Nb(OEt)_5$ do not meet this requirement.

Sol-gel processing is another approach that has many advantages for depositing layers of the tantalum and niobium oxide compounds. In sol-gel processing, a starting reagent solution is combined with water whereupon the reagents hydrolyze to precipitate the oxides. Control of stoichiometry and crystal quality are more problematic than with chemical vapor deposition, but sol-gel processing has advantages in terms of cost and simplicity of required apparatus. Appropriate reagents must be available as starting materials for each of the metal oxides. Many of the same criteria as apply to CVD reagents are appropriate for sol-gel reagents as well.

Accordingly, it is an object of the present invention to provide niobium and tantalum reagents suitable for the preparation of ceramic oxide films. Such reagents are sufficiently volatile to be used in CVD processes and decompose to deposit the desired oxide at temperatures that are low enough to be compatible with semiconductor device materials and processes, and also may be used in sol-gel processing methods to deposit the desired oxide. The tantalum and niobium reagents of the present invention are compatible with beta-diketonate source reagents.

It is another object of the present invention to provide methods of making these niobium and tantalum reagents.

Other objects and advantages of the present invention will be more fully apparent from the ensuing disclosure and appended claims.

SUMMARY OF THE INVENTION

The present invention relates to beta-diketonate alkoxide compounds, comprising compounds having niobium or tantalum complexed to at least one alkoxide ligand and at least one beta-diketonate ligand. The general formula of these compounds is:

$$M(OR^1)_x(R^2-C(G)-CH-C(G)-R^3)_{5-x}$$

where M is niobium or tantalum, G is oxygen or sulfur, and x=1–4. $R^1$ is C1–C6 hydrocarbyl or fluoroalkyl. $R^2$ and $R^3$ are independently selected C2–C6 hydrocarbyl, C1–C6 alkoxy, or C2–C6 fluoroalkyl groups, wherein hydrocarbyl groups may be selected from alkyl, cycloalkyl, alkenyl or aryl groups of 2 through 6 carbons and fluoroalkyl groups may be selected from perfluoroalkyls of 2 through 6 carbons. $R^1$ is preferably C1–C16 alkyl, preferably methyl, ethyl, propyl, n-propyl, i-propyl, n-butyl, s-butyl, or t-butyl, and most preferably ethyl, i-propyl, or t-butyl. $R^2$ and $R^3$ are preferably selected from the C2–C6 alkyl or cycloalkyl groups t-butyl, s-butyl, i-propyl, cyclohexyl, or neopentyl, and most preferably t-butyl, s-butyl, or isopropyl.

Generalized chemical equations that illustrate the synthetic methods that may be used to prepare the compounds of the present invention are, where bdk refers to beta-diketonate or beta-ketoester and R is a hydrocarbyl or fluoroalkyl group:

$$M(OR)_5 + nbdkH \rightarrow M(OR)_{5-n}(bdk)_n + nROH$$

$$M(OR)_{5-n}(bdk)_n + xs\ R'OH \rightarrow M(OR')_{5-n}(bdk)_n + (5-n)ROH$$

$$MCl_5 + nbdkH \rightarrow MCl_{5-n}(bdk)_n + nHCl$$

$$MCl_{5-n}(bdk)_n + xsROH \rightarrow M(OR)_{5-n}(bdk)_n + (5-n)HCl$$

In the latter two reactions, base may be added to drive the reaction to the right. Other aspects and features of the invention will be more fully apparent from the ensuing disclosure and appended claims.

DESCRIPTION OF THE DRAWINGS

The Figure is a schematic representation of a chemical vapor deposition apparatus useful for the deposition of niobium or tantalum containing films by the method of the present invention.

DETAILED DESCRIPTION OF THE INVENTION, AND PREFERRED EMBODIMENTS THEREOF

The novel niobium and tantalum compounds of the present invention have the formulae:

$$M(OR^1)_x(R^2-C(G)-CH-C(G)-R^3)_{5-x}$$

where M is niobium or tantalum, G is oxygen or sulfur, and x=1–4. $R^1$ is C1–C6 hydrocarbyl or fluoroalkyl. $R^2$ and $R^3$ are independently selected C2–C6 hydrocarbyl, C1–C6 alkoxy, or C2–C6 fluoroalkyl groups, wherein hydrocarbyl groups may be selected from alkyl, cycloalkyl, alkenyl or aryl groups of 2 through 6 carbons and fluoroalkyl groups may be selected from perfluoroalkyls of 2 through 6 carbons. $R^1$ is preferably C1–C6 alkyl, preferably methyl, ethyl, propyl, n-propyl, i-propyl, n-butyl, s-butyl, or t-butyl, and most preferably ethyl, i-propyl, or t-butyl. $R^2$ and $R^3$ are preferably selected from the C2–C6 alkyl or cycloalkyl groups t-butyl, s-butyl, i-propyl, cyclohexyl, or neopentyl, and most preferably t-butyl, s-butyl, or isopropyl.

The choices of $R^1$, $R^2$, and $R^3$ substituents are dictated by the requirements of the film-forming techniques that the reagents are designed for. In the design of chemical vapor deposition source reagents, considerations can include solubility in the convenient and commonly used solvent systems for liquid delivery systems as described in U.S. Pat. No. 5,204,314; volatility for ease of delivery into a CVD reactor; stability to oxidation, hydrolysis, and thermal decompositionl; compatibility with other CVD source reagents employed in the system for delivery of other elements of the desired oxide compound; and elemental and chemical purity. Similar constraints are applicable in sol-gel processing.

In many applications the source reagent is used in a chemical vapor deposition process along with source reagents for delivery of other elements. Upon heating the reagents to vaporize and deliver them to the reactor or under the high temperature conditions present in the CVD reactor, the metal complexes may undergo ligand exchange reactions. If the products of such ligand exchange reactions are involatile, the result may be premature nucleation and formation of particulate species in the reactor, in the lines leading from the source reservoir(s) to the reactor, or in the source reservoir itself, if more than one reagent is held in the same reservoir. Thus stability to ligand exchange reactions in the solvent/reagent system of choice is an important consideration.

Therefore, the compounds of the present invention incorporate one or more alkoxide ligands as well as one or more beta-diketonate ligands. The alkoxide and beta-diketonate ligands are selected to optimize the volatility of the resulting complex, consistent with the steric contraints presented by bulky groups such as t-butyl or neopentyl.

Previously described alkoxide/beta-diketonate complexes of tantalum and niobium have utilized only the simpler beta-diketonate ligands such as acetylacetonate or benzoylacetonate, as for example, Ta(OEt)$_4$(acac) (*J. Less Common Metals*, 1965, 8, 339). Such complexes do not have optimal characteristics of chemical vapor deposition reagents. In particular for the Group II or early transition element source reagents, use of the bulkier beta-diketonate ligands such as thd leads to a more volatile complex. In order for the the tantalum and niobium reagents to be compatible in CVD processes with these less volatile Group II and early transition element source reagents, e.g. Ba(thd)$_2$, Sr(thd)$_2$, and Ba(fod)$_2$, they should incorporate the same diketonate ligands. Otherwise, deleterious ligand exchange reactions can occur. In addition, the smaller ligands such as acac may not render the complexes sufficiently soluble in the solvent systems usually employed in liquid delivery. Thus the reagents of the present invention incorporate the diketonate ligands that have bulkier substituents, for example, t-butyl or isopropyl.

The Figure is a schematic representation of a chemical vapor deposition apparatus useful for the deposition of niobium or tantalum containing films by the method of the present invention. Niobium or tantalum compounds of the type described herein are dissolved in appropriate solvent(s) and the solution(s) are contained, at ambient temperature, in one or more liquid reservoirs (1). Metalorganic precursors for simultaneous deposition of other elements are also in the solution reservoirs (1). These other elements may include Ba, Sr, Bi, Ti, etc., as needed to deposit ferroelectric or other complex oxide compounds described above. The chemical composition of the niobium or tantalum reagents that are claimed renders them stable in the presence of these other metalorganic compounds in either the liquid or gas phase, i.e. exchange of ligands is prevented. The chemical vapor deposition reactor (8) contains a substrate (7), which is typically heated prior to film deposition, although energy to stimulate chemical ractions may be provided in other ways such as gas phase radicals, energetic particles or photons. The atmosphere in the reactor may contain oxygen, nitrous oxide and other gases (both reactive or inert), and the pressure in the vessel may be either at or below atmospheric pressure.

When the reactor is conditioned appropriately, source reagent liquids in the reservoirs (1) flow to a high precision liquid pump (3) through a valve (2). The pump then supplies the liquid solution to a hot vaporization zone (4), heated to temperature sufficiently high to flash vaporize the reagents, e.g. in the range of 140°–260° C., at which point the solvent and the niobium, tantalum and other reagents are transformed into the gas phase either by evaporation or sublimation. The gas-phase reagents then flow to the substrate (7) via a gas line (5) which is heated. When the gaseous reagents reach the substrate (7), which is heated to temperatures sufficiently high to decompose the source reagents, e.g. in the range of 250° C. to 1000° C. depending on the identity of the source reagent, they chemically decompose and react to form the desired solid compound in the form of a thin film on the substrate. By-products from these reactions are removed from the reactor (7) by a suitable exhaust (8).

Generalized chemical equations that illustrate the synthetic methods that may be used to prepare the compounds of the present invention are, where bdk refers to beta-diketonate or beta-ketoester and R is a hydrocarbyl or fluoroalkyl group:

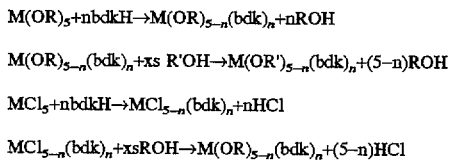

$M(OR)_5 + nbdkH \rightarrow M(OR)_{5-n}(bdk)_n + nROH$ $M(OR)_{5-n}(bdk)_n + xs\ R'OH \rightarrow M(OR')_{5-n}(bdk)_n + (5-n)ROH$ $MCl_5 + nbdkH \rightarrow MCl_{5-n}(bdk)_n + nHCl$ $MCl_{5-n}(bdk)_n + xsROH \rightarrow M(OR)_{5-n}(bdk)_n + (5-n)HCl$ In the latter two reactions, base may be added to drive the reaction to the right.

The following non-limiting examples illustrate the synthesis of compounds of the present invention and their use to form films and layers.

EXAMPLE 1

Synthesis of Ta(OEt)$_4$($\eta^2$-thd)

One equivalent (33.89 g) of 2,2,6,6-tetramethyl-3,5-heptanedione (Hthd) was added directly to 74.6 g Ta(OEt)$_5$ in a 500 mL Schlenk flask; both starting materials were obtained commercially. The vessel was heated to 65° C. under a slow nitrogen purge to a bubbler. After 2 hours the ethanol generated was removed in vacuo to yield 99.8 g of the colorless liquid Ta(OEt)$_4$($\eta^2$-thd) in quantitative yield, which solidified upon cooling. The compound melted at 26° C. and boiled at approximately 80° C. at 140 mtorr. The $^1$H and $^{13}$C NMR spectra in benzene-d$_6$ were consistent with an octahedral structure composed of two ethoxide ligands in axial positions and a second set of cis-ethoxide ligands in the equatorial plane across from the bidentate $\beta$-diketonate: $\delta$5.81 (s, 1 H, CH), 4.72 (q, 4 H, CH$_2$), 4.20 (q, 4 H, CH$_2$), 1.34 (tr, 6 H, CH$_3$), 1.14 (tr, 6 H, CH$_3$), 1.13 (s, 18 H, t-Bu); $^{13}$C{$^1$H} NMR (C$_6$D$_6$) $\delta$199.9 (CO), 92.9 (CH$_{diket}$), 68.8 (CH$_2$CH$_3$), 65.4 (CH$_2$CH$_3$), 40.9 (CMe$_3$), 28.3 (CMe$_3$), 19.6 (CH$_2$CH$_3$), 19.0 (CH$_2$CH$_3$).

EXAMPLE 2

Synthesis of Ta(O-i-Pr)$_4$($\eta^2$-thd)

A nine-fold excess of isopropanol (170 mL) was added to 33.6 g Ta(OEt)$_4$($\eta^2$-thd). The solution was heated at 60° C. for 45 min, following which the volatiles were removed in vacuo. The ligand exchange procedure was repeated a second time to yield 36.8 g of white, crystalline Ta(O-i-Pr)$_4$($\eta^2$-thd) in quantitative yield. The product was purified by sublimation at 100° C. at 150 mtorr. The compound melted at 149° C. The $^1$H and $^{13}$C NMR spectra in benzene-d$_6$ were consistent with an octahedral structure composed of two isopropoxide ligands in axial positions and a second set of cis-isopropoxide ligands in the equatorial plane across from the bidentate $\beta$-diketonate: $\delta$5.81 (s, 1 H, CH), 5.10 (sept, 2 H, CH), 4.51 (sept, 2 H, CH), 1.38 (d, 12 H, Me), 1.20 (d, 12 H, Me), 1.17 (s, 18 H, t-Bu); $^{13}$C{$^1$H} NMR (C$_6$D$_6$) $\delta$199.4 (CO), 93.0 (CH$_{diket}$), 75.0 (CHMe$_2$), 71.4 (CHMe$_2$), 40.8 (CMe$_3$), 28.3 (CMe$_3$), 26.4 (CHMe$_2$), 25.8 (CHMe$_2$).

EXAMPLE 3

Synthesis of Nb(OEt)$_4$($\eta^2$-thd)

The procedure of Example 1 is followed, using Nb(OEt)$_5$ as starting material rather than the tantalum ethoxide. One equivalent of 2,2,6,6-tetramethyl-3,5-heptanedione (Hthd) is added directly to Nb(OEt)$_5$ in a Schlenk flask. The vessel is heated to about 65° C. under a slow nitrogen purge to a bubbler. After 2 hours the ethanol generated is removed in vacuo to yield Nb(OEt)$_4$($\eta^2$-thd) in quantitative yield.

EXAMPLE 4

Synthesis of Nb(O-i-Pr)$_4$($\eta^2$-thd)

A nine-fold molar excess of isopropanol is added to Nb(OEt)$_4$($\eta^2$-thd). The resulting solution is heated at 60° C. for 45 min, following which the volatiles are removed in vacuo. The ligand exchange procedure is repeated a second time to yield solid Nb(O-i-Pr)$_4$($\eta^2$-thd) in quantitative yield. The product is purified by sublimation at 100° C. at 150 mtorr.

EXAMPLE 5

Deposition of Niobia Film

Nb(O-i-Pr)$_4$($\eta^2$-thd) is used to deposit Nb$_2$O$_5$ ("niobia") on a silicon wafer held at 400° C. in a CVD reactor. The Nb reagent is contained in a vessel ("bubbler") held at 185° C. and Ar gas is flowed through the vessel at 100 sccm. Pressure in the "bubbler" is controlled at 80 torr using a manual throttle valve. Oxygen is flowed to the reactor through a separate manifold at 300 sccm. Total pressure in the reactor is 1 torr and partial pressure of the Nb reagent in the reactor is 0.03 torr. Deposition rate is approximately 0.04 μm/minute.

EXAMPLE 6

Deposition of Tantala Film

Ta(O-i-Pr)$_4$(thd) is used to deposit Ta$_2$O$_5$ (tantala) on a fused silica (glass) envelope of a high entensity lamp by chemical vapor deposition. The glass surface is held at 450° C. in a CVD reactor. The Ta(O-i-Pr)$_4$(thd) compound is dissolved in an organic solvent and this liquid solution is pumped to a vaporization zone of the reactor held at 200° C. where Ar carrier gas is also introduced at 100 sccm. At the vaporizer zone the solvent evaporates, the Ta compound sublimes and the gaseous reagents and Ar then flow to the chemical vapor deposition reactor. Oxygen is flowed to the reactor through a separate manifold at 300 sccm. Total pressure in the reactor is 1 torr and the deposition rate is 0.065 μm/minute.

EXAMPLE 7

Deposition of Nb:BST

Nb(O-i-Pr)$_4$($\eta^2$-thd) is used to deposit Ba$_{1-x}$Sr$_x$Ti$_{1-y}$Nb$_y$O$_3$ (Nb:BST) on a platinum metal layer on a silicon wafer in a CVD reactor. The metal layer will act as a bottom electrode in a capacitor and the Nb:BST film will have a high dielectric constant with dc low leakage current density. The platinum surface is held at 650° C. Nb(O-i-Pr)$_4$($\eta^2$-thd) reagent is dissolved in an organic solvent along with Ba(thd)$_2$-tetraglyme, Sr(thd)$_2$-tetraglyme and Ti(OPr)$_2$(thd)$_2$, and this liquid solution is pumped to a vaporization zone held at 220° C. where Ar carrier gas is also introduced at 600 sccm. The solution is stable and there is no ligand exchange between the metallorganic compounds either in the liquid or gas phase. At the vaporization zone the solvent evaporates and the Ba, Sr, Ti and Nb compounds sublime. The gaseous reagents and Ar then flow to the CVD reactor. A mixture of oxygen and nitrous oxide is flowed to the reactor through a separate manifold at 300 sccm each. Total pressure in the reactor is 0.700 torr and the (Nb:BST) is deposited at a rate of 0.0165 μm/minute.

EXAMPLE 8

Deposition of Bi$_2$SrTa$_2$O$_9$

Ta(O-i-Pr)$_4$(thd) is used to deposit Bi$_2$SrTa$_2$O$_9$ on platinum metal layer on a silicon wafer in a CVD reactor. The Bi$_2$SrTa$_2$O$_9$ film will form a ferroelectric capacitor with remanent polarization that can be switched greater than $10^{12}$ times. The Bi$_2$SrTa$_2$O$_9$ is deposited at 650° C. Ta(O-i-Pr)$_4$(thd) is dissolved in an organic solvent along with triphenylbismuth and Sr(thd)$_2$-tetraglyme and this liquid solution is pumped to a vaporization zone held at 200° C. where Ar carrier gas is also introduced at 100 sccm. The solution is stable and there is no ligand exchange between the metallorganic compounds either in the liquid or gas phase. At the vaporization zone the solvent evaporates and the Bi, Sr, Na compounds sublime. The gaseous reagents and Ar then flow to the chemical vapor deposition reactor. A mixture of oxygen and nitrous oxide is flowed to the reactor through a separate manifold at 300 sccm each. Total pressure in the reactor is 2.1 torr and the Bi$_2$SrTa$_2$O$_9$ is deposited at a rate of 0.0165 μm/minute.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A process for forming a tantalum- or niobium-containing coating on a substrate, comprising the steps of:

providing a vapor of a compound of the formula:

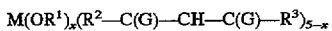

wherein:

x is from 1–4;

M is tantalum or niobium;

G is oxygen or sulfur;

R$^1$ is C$_1$–C$_6$ hydrocarbyl or fluoroalkyl; and

R$^2$ and R$^3$ are independently selected from C$_2$–C$_6$ hydrocarbyl, C$_2$–C$_6$ fluoroalkyl and C$_1$–C$_6$ alkoxy groups, with the provisos that when G is oxygen:

R$^2$ and R$^3$ are not simultaneously both phenyl when either one of R$^2$ and R$^3$ is ethoxy, the other is not phenyl;

when either one of R$^2$ and R$^3$ is t-butyl, the other is not heptafluoropropyl;

when either one of R$^2$ and R$^3$ is ethyl, the other is not methyl; and exposing said vapor to the substrate for deposition of said tantalum- or niobium-containing coating thereon.

2. A process according to claim 1, wherein the substrate is held at a temperature of 250° C. to 1000° C.

3. A process according to claim 1, additionally comprising directing said vapor to said substrate in a carrier gas.

4. A process according to claim 1, wherein said vapor is provided by flash vaporization of a composition comprising said compound and a solvent therefor.

5. A process according to claim 1, wherein M is tantalum.

6. A process according to claim 1, wherein M is niobium.

7. A process according to claim 1, wherein G is oxygen.

8. A process according to claim 1, wherein R1 is selected from the group consisting of C1–C4 alkyls.

9. A process according to claim 1, wherein the compound is tantalum tetraisopropoxytetramethylheptanedionate.

10. A process according to claim 1, wherein the compound is tantalum tetraethoxytetramethylheptanedionate.

11. A process according to claim 1, wherein the compound is selected from the group consisting of niobium tetraisopropoxytetramethylheptanedionate and niobium tetraethoxytetramethylheptanedionate.

12. A process according to claim 1, wherein the tantalum- or niobium-containing coating comprises a complex oxide compound.

13. A process according to claim 4, wherein said flash vaporization is carried out at a temperature of from 140° to 260° C.

14. A process according to claim 1, wherein the step of exposing said vapor to the substrate is conducted in the presence of a gas selected from the group consisting of oxygen and nitrous oxide.

15. A process according to claim 1, wherein said coating is SrBi$_2$Ta$_2$O$_9$.

16. A process according to claim 1, wherein said coating is SrBi$_2$Nb$_2$O$_9$.

17. A process according to claim 1, wherein the tantalum- or niobium-containing coating comprises a ferroelectric oxide compound.

18. A process for forming a tantalum- or niobium-containing coating, selected from the group consisting of SrBi$_2$Ta$_2$O$_9$ and SrBi$_2$Nb$_2$O$_9$, on a substrate, comprising the steps of:

providing a vapor of a compound of the formula:

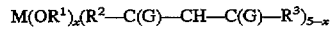

wherein:

x is from 1–4;

M is tantalum or niobium;

G is oxygen or sulfur;

R$^1$ is C$_1$–C$_6$ hydrocarbyl or fluoroalkyl; and

R$^2$ and R$^3$ are independently selected from C$_2$–C$_6$ hydrocarbyl, C$_2$–C$_6$ fluoroalkyl and C$_1$–C$_6$ alkoxy groups, with the provisos that when G is oxygen:

R$^2$ and R$^3$ are not simultaneously both phenyl;

when either one of R$^2$ and R$^3$ is ethoxy, the other is not phenyl;

when either one of R$^2$ and R$^3$ is t-butyl, the other is not heptafluoropropyl;

when either one of R$^2$ and R$^3$ is ethyl, the other is not methyl; and exposing said vapor to the substrate for deposition of said tantalum or niobium-containing coating thereon.

19. A process according to claim 18, wherein said coating is SrBi$_2$Ta$_2$O$_9$.

20. A process according to claim 18, wherein said coating is SrBi$_2$Nb$_2$O$_9$.

* * * * *